United States Patent
Krishna Rao et al.

(10) Patent No.: US 9,715,622 B2
(45) Date of Patent: Jul. 25, 2017

(54) SYSTEM AND METHOD FOR PREDICTING NEUROLOGICAL DISORDERS

(71) Applicant: Cognizant Technology Solutions India Pvt. Ltd, Chennai (IN)

(72) Inventors: Geelapaturu Subrahmanya Venkata Radha Krishna Rao, Chennai (IN); Kuhelee Roy, Kolkata (IN); Savarimuthu Margret Anouncia, Tamil Nadu (IN)

(73) Assignee: COGNIZANT TECHNOLOGY SOLUTIONS INDIA PVT. LTD., Chennai (IN)

( * ) Notice: Subject to any disclaimer, the term of this patent is extended or adjusted under 35 U.S.C. 154(b) by 0 days.

(21) Appl. No.: 14/797,365

(22) Filed: Jul. 13, 2015

(65) Prior Publication Data
US 2016/0189371 A1    Jun. 30, 2016

(30) Foreign Application Priority Data
Dec. 30, 2014 (IN) .......................... 6745/CHE/2014

(51) Int. Cl.
G06K 9/00 (2006.01)
G06T 7/00 (2017.01)
(Continued)

(52) U.S. Cl.
CPC .......... G06K 9/00348 (2013.01); A61B 5/112 (2013.01); A61B 5/1128 (2013.01);
(Continued)

(58) Field of Classification Search
CPC ...... G06T 7/0012; G06T 7/246; A61B 5/4076
See application file for complete search history.

(56) References Cited

U.S. PATENT DOCUMENTS

2006/0023949 A1* 2/2006 Saito .................. G06K 9/00355
382/217
2007/0153005 A1   7/2007 Asai
(Continued)

OTHER PUBLICATIONS

Poleg. "Head Motion Signatures from Egocentric Videos" The Hebrew University of Jerusalem, Israel, 15 page.*
(Continued)

Primary Examiner — Oneal R Mistry
(74) Attorney, Agent, or Firm — Cantor Colburn LLP

(57) ABSTRACT

A method and system for predicting neurological disorders is provided. The method comprises receiving videos of individuals and detecting Regions of Interest (ROI) in video frames. The method further comprises determining a Motion Vector (MV) for each ROI in a set of successive frames and comparing value of the determined MV with pre-stored values. Furthermore, the method comprises identifying a MV matching a pre-stored value thereby identifying a ROI and a frame corresponding to the identified MV, wherein the pre-stored value indicates onset of an expression. Also, the method comprises determining MVs for the identified ROI in subsequent sets of successive frames and comparing value of the determined MVs with a pre-stored value of MV corresponding to peak and offset of the indicated expression. The method further comprises identifying the frame corresponding to the peak and offset of the indicated expression and generating pictorial representation for predicting neurological disorders.

15 Claims, 10 Drawing Sheets

(51) Int. Cl.
  *A61B 5/00*     (2006.01)
  *A61B 5/11*     (2006.01)
  *A61B 5/16*     (2006.01)
  *H04N 19/503*   (2014.01)
  *H04N 19/17*    (2014.01)
  *G06K 9/32*     (2006.01)
  *G06T 7/246*    (2017.01)

(52) U.S. Cl.
  CPC ............ *A61B 5/165* (2013.01); *A61B 5/4076* (2013.01); *A61B 5/7275* (2013.01); *G06K 9/00362* (2013.01); *G06K 9/3233* (2013.01); *G06T 7/0012* (2013.01); *G06T 7/246* (2017.01); *H04N 19/17* (2014.11); *H04N 19/503* (2014.11); *A61B 5/4082* (2013.01); *A61B 5/7257* (2013.01); *A61B 5/7267* (2013.01); *A61B 2576/00* (2013.01); *G06T 2207/10016* (2013.01); *G06T 2207/20081* (2013.01); *G06T 2207/30016* (2013.01); *G06T 2207/30196* (2013.01)

(56) References Cited

U.S. PATENT DOCUMENTS

| | | |
|---|---|---|
| 2008/0037841 A1 | 2/2008 | Ogawa |
| 2009/0285456 A1 | 11/2009 | Moon |
| 2012/0093370 A1* | 4/2012 | Ding ............... G06K 9/6215 382/106 |
| 2012/0314064 A1* | 12/2012 | Liu ............... G06K 9/00771 348/143 |
| 2014/0242560 A1 | 8/2014 | Movellan |
| 2016/0171293 A1* | 6/2016 | Li ............... G06K 9/00355 382/103 |

OTHER PUBLICATIONS

Body Language vs. Micro-Expressions Blog, published in Psychology Today, Internet: URL: https://www.psychologytoday.com/blog/spycatcher/201112/body-language-vs-micro-expressions.

Marian Bartlett, et al., Emotient Blog, Internet: URL: http://www.emotient.com/blog/?page=1.

Marian Bartlett, et al., Emotient Blog, Internet: URL: http://www.emotient.com/blog/?page=2.

* cited by examiner

SYSTEM AND METHOD FOR PREDICTING NEUROLOGICAL DISORDERS

CROSS REFERENCE TO RELATED APPLICATION

This application is related to and claims the benefit of Indian Patent Application Number 6745/CHE/2014 filed on Dec. 30, 2014, the contents of which are herein incorporated by reference in their entirety.

FIELD OF THE INVENTION

The present invention relates generally to predicting neurological disorders. More particularly, the present invention provides a system and method for predicting neurological disorders using one or more videos of one or more individuals.

BACKGROUND OF THE INVENTION

Depression or the state of low mood adversely affects thoughts and behavior of humans and gives rise to disability in people. People with depressed mood lose interest in their lives and their activities. Depression also escalates risks of patients suffering from other health problems and may even obstruct the line of treatment for such patients. For example, risk associated with a person suffering from neurological health problems is escalated when he/she is also suffering from depression. Further, in several instances, depression can also lead to various neurological disorders that may cause gait abnormalities. It is therefore important to identify and monitor patients suffering from depression. Also, it is equally important to determine and analyze if the patient is showing symptoms of neurological disorders and gait abnormalities.

Various approaches are known in the art for monitoring patients for depression and neurological disorders. A general approach include diagnosis of an individual under depression by the aid of existing interview tools comprising pre-set questionnaire that may be administered by a physician. For example, the physician may ask the patient if he/she has been feeling low, depressed or hopeless in the past few weeks or if he/she had suicidal thoughts. The physician may also enquire about his/her sleep pattern and energy levels and ask if the patient prefers to stay at home rather than going out and/or doing new things in order to determine if the patient is suffering from depression.

Similarly, abnormal gait patterns such as loss of balance, abnormal walking and speech patterns in humans can be detected using sensors, biometric devices and other clinical devices or equipment. The abnormal gait patterns can also be detected using various available methods including determining alterations in gait speed, head turns, clearing obstacle, climbing steps; measuring time taken to walk in different situations such as walking on a hard floor or on a carpeted floor, stepping over a brick-like object, walking around an object etcetera; evaluating performance of the patient along a series of simulations of functional mobility tasks or situations in home environment; and distinguishing between fallers and non-fallers.

The afore-mentioned approaches clearly indicate that physical presence of a doctor or a physician is always needed to carry out the detection of depression and gait abnormalities in patients. For example, the use of interview tools comprising pre-set questionnaire is dependent on the questionnaire between a doctor and a patient and the response from the patient in form of text to extract the emotion of the subject. The methods known for detection of abnormal gait patterns also involve presence of a physician or a doctor. This certainly does not effectively solve the widespread issues of detection of depression and gait abnormality. The prevalence of these issues across the world necessitates the need of remote management systems and methods for automatic detection of depression and abnormal gait pattern wherein a computer-aided diagnosis of depression and abnormal gait pattern is used and subsequently a report is generated based on the initial symptoms visible from the facial expressions and gait of an individual. The remotely managed systems and methods for carrying out the detection of depression and gait abnormalities in individuals do not require clinical equipment or physical presence of physicians.

Various computer-aided solutions are known in the art for detecting and monitoring depressions and gait abnormality in individuals. However, these solutions are very slow and fail to precisely detect expressions and are unable to identify real facial motion such as fine motions in the lip and eye regions. These solutions also do not identify dominant regions of motion that largely contributes to the analysis of depression and abnormal gait patterns. The available solutions further fail to provide remote management of patients suffering from depression and gait abnormality.

In light of the above, there is a need for a system and method for predicting one or more neurological disorders. Further, there is a need for a system and method to identify depression and abnormal gait patterns in individuals remotely or locally. Furthermore, there is a need for a computer-aided system and method that eliminates the requirement of questionnaire from physicians, sensors, and other medical equipment. In addition, there is a need for a system and method to identify and monitor fine movements and dominant regions of motion that largely contributes in identifying and monitoring depression and abnormal gait patterns in patients.

SUMMARY OF THE INVENTION

A method and system for predicting one or more neurological disorders is provided. The method comprises receiving, via a processor configured to execute program instructions stored in a memory, one or more videos of one or more individuals. The method further comprises splitting, via the processor, the one or more videos into one or more frames. Furthermore, the method comprises detecting, via the processor, one or more regions of interest in each of the one or more frames. In addition, the method comprises analyzing, via the processor, each of the one or more regions of interest in each of the one or more frames by determining a motion vector for each of the one or more regions of interest in a set of successive frames; and comparing value of the determined motion vector for each of the one or more regions of interest with corresponding pre-stored values, wherein the pre-stored values for the motion vector for each of the one or more regions are pre-stored in a database. The method further comprises identifying, via the processor, at least one motion vector, from the determined motion vectors, that matches with the pre-stored value of a motion vector thereby identifying a region of interest and a frame corresponding to the identified at least one motion vector, wherein the pre-stored value indicates onset of an expression. Also, the method comprises determining, via the processor, one or more motion vectors for the identified region of interest in subsequent sets of successive frames. The method further comprises comparing, via the processor, value of the one or more determined motion vectors for the identified region of interest with at least one of a pre-stored value of motion vector corresponding to peak and a pre-stored value of motion vector corresponding to offset of the indicated expression. The method also comprises identifying, via the processor, the frame corresponding to the at least one of: the peak of the indicated expression and the offset of the indicated expression. In addition, the method comprises generating, via the processor, a pictorial representation of the one or more videos depicting at least one of: the onset, peak and offset of the indicated expression of the one or more individuals captured in the one or more videos for predicting the one or more neurological disorders.

In an embodiment of the present invention, the one or more expressions include at least one of: happy, content, sad, disgust, surprise, clueless and angry. In an embodiment of the present invention, the detected one or more regions of interest include at least one of: eyes, cheeks, nose, lips, ears, eyebrows, hands, arms, torso, legs and feet. In an embodiment of the present invention, the regions of interest are detected using Viola-Jones algorithm. In an embodiment of the present invention, the motion vector for each of the one or more regions of interest in a set of successive frames is determined using optical flow algorithm. Further, the optical flow algorithm uses Horn-Schunck method for determining the motion vector. In an embodiment of the present invention, the one or more individuals are speaking while the one or more videos are being captured.

The system for predicting one or more neurological disorders comprises a video acquisition module configured to receive one or more videos of one or more individuals and split the one or more videos into one or more frames. The system further comprises a region of interest detection module configured to detect one or more regions of interest in each of the one or more frames. Furthermore, the system comprises a video processing module configured to analyze each of the one or more detected regions of interest in each of the one or more frames, wherein the video processing module comprises a feature extraction module configured to determine a motion vector for each of the one or more regions of interest in a set of successive frames and a comparator configured to compare value of the determined motion vector for each of the one or more regions of interest with corresponding pre-stored values, wherein the pre-stored values for the motion vector for each of the one or more regions are stored in a training module. The feature extraction module is further configured to identify at least one motion vector, from the determined motion vectors, that matches with the pre-stored value of a motion vector thereby identifying a region of interest and a frame corresponding to the identified at least one motion vector, wherein the pre-stored value indicates onset of an expression; and determine one or more motion vectors for the identified region of interest in subsequent sets of successive frames. The comparator is further configured to compare value of the one or more determined motion vectors for the identified region of interest with at least one of a pre-stored value of motion vector corresponding to peak and a pre-stored value of motion vector corresponding to offset of the indicated expression; and identify the frame corresponding to the at least one of: the peak of the indicated expression and the offset of the indicated expression. The system further comprises a testing module configured to generate a pictorial representation of the one or more videos depicting at least one of: the onset, peak and offset of the indicated expression of the one or more individuals captured in the one or more videos for predicting the one or more neurological disorders.

A method for predicting one or more neurological disorders, via a processor configured to execute program instructions stored in a memory, is provided. The method comprises receiving, via the processor, one or more videos of one or more individuals. The method further comprises splitting, via the processor, the one or more videos into one or more frames. Furthermore, the method comprises detecting, via the processor, one or more regions of interest in each of the one or more frames. The method also comprises analyzing, via the processor, each of the one or more regions of interest in each of the one or more frames by determining one or more features, related to one or more gait patterns, corresponding to each of the one or more regions of interest in a set of successive frames; and comparing values of the determined one or more features with corresponding pre-stored values of the one or more features of each of the one or more regions of interest. In addition, the method also comprises identifying a gait pattern of the one or more individuals based on the comparison, wherein at least one compared value matches a corresponding pre-stored value of at least one feature, and further wherein the matched pre-stored value of the at least one feature is associated with the identified gait pattern that is used to predict the one or more neurological disorders. In an embodiment of the present invention, the one or more videos are captured when the one or more individuals are involved in an activity including walking, running, and any other activity. In an embodiment of the present invention, the detected one or more regions of interest include at least one of: upper body, lower body, arms, legs and feet. In an embodiment of the present invention, the one or more features related to the one or more gait patterns include at least one of: motion, posture, arm swing velocity and body balance. In an embodiment of the present invention, the one or more gait patterns include: parkinsonian gait, scissor gait, spastic gait, steppage gait and normal gait.

A computer program product for predicting one or more neurological disorders is provided. The computer program product comprises a non-transitory computer-readable medium having computer-readable program code stored thereon, the computer-readable program code comprising instructions that when executed by a processor, cause the processor to receive one or more videos of one or more individuals. The processor further splits the one or more videos into one or more frames. Furthermore, the processor detects one or more regions of interest in each of the one or more frames. The processor also analyzes each of the one or more regions of interest in each of the one or more frames by determining a motion vector for each of the one or more regions of interest in a set of successive frames and comparing value of the determined motion vector for each of the one or more regions of interest with corresponding pre-stored values, wherein the pre-stored values for the motion vector for each of the one or more regions are pre-stored in a database. The processor further identifies at least one motion vector, from the determined motion vectors, that matches with a pre-stored value of a motion vector thereby identifying a region of interest and a frame corresponding to the identified at least one motion vector, wherein the pre-stored value indicates onset of an expression. Furthermore, the processor determines one or more motion vectors for the identified region of interest in subsequent sets of successive frames. The processor also compares value of the one or more determined motion vectors for the identified region of interest with at least one of a pre-stored value of motion vector corresponding to peak and a pre-stored value of motion vector corresponding to offset of the indicated expression. The processor then identifies the frame corresponding to the at least one of: the peak of the indicated expression and the offset of the indicated expression. In addition, the processor generates a pictorial representation of the one or more videos depicting at least one of: the onset, peak and offset of the indicated expression of the one or more individuals captured in the one or more videos for predicting the one or more neurological disorders.

BRIEF DESCRIPTION OF THE ACCOMPANYING DRAWINGS

The present invention is described by way of embodiments illustrated in the accompanying drawings wherein.

DETAILED DESCRIPTION OF THE INVENTION

A system and method for predicting neurological disorders is described herein. The invention provides a system and method to identify depression and abnormal gait patterns in individuals remotely or locally. Further, the invention provides a computer-aided system and method that eliminates the requirement of questionnaire from physicians, sensors, and other medical equipment. In addition, the invention provides a system and method to identify and monitor fine movements and dominant regions of motion that largely contribute in identifying and monitoring depression and abnormal gait patterns in patients.

The following disclosure is provided in order to enable a person having ordinary skill in the art to practice the invention. Exemplary embodiments are provided only for illustrative purposes and various modifications will be readily apparent to persons skilled in the art. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

The present invention would now be discussed in context of embodiments as illustrated in the accompanying drawings.

Figure 1:
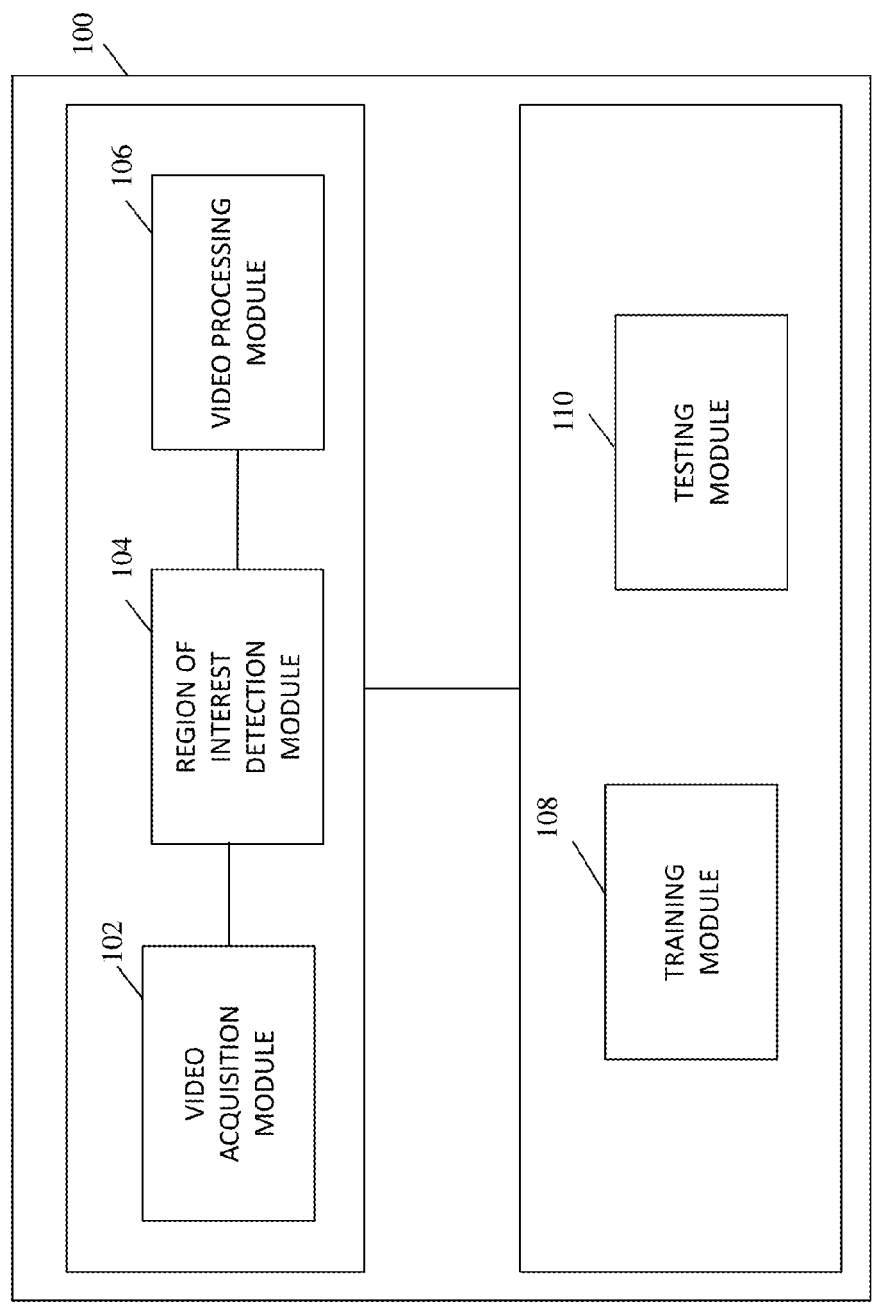
FIG. 1 is a block diagram illustrating a system for predicting one or more neurological disorders, in accordance with an embodiment of the present invention.

FIG. 1 is a block diagram illustrating a system 100 for predicting one or more neurological disorders, in accordance with an embodiment of the present invention. The system 100 comprises a video acquisition module 102, a region of interest detection module 104, a video processing module 106, a training module 108 and a testing module 110.

The video acquisition module 102 is configured to capture the one or more videos of the one or more individuals. The video acquisition module 102 is also configured to receive the one or more videos of the one or more individuals from one or more electronic devices. In an embodiment of the present invention, the one or more videos of the one or more individuals include videos of subjects whose expressions are to be analyzed and based on the analysis disorder has to be predicted. Further, the videos may be captured when the individual/subject in the video is involved in an activity including, but not limited to, speaking, walking, running and/or any other activity. In an embodiment of the present invention, the one or more electronic devices include, but not limited to, a mobile phone, a tablet, a camera or any other device having a camera capable of capturing videos.

The video acquisition module 102 balances the resolution and the illumination of the one or more videos received from various sources. This helps in maintaining the quality of the one or more videos for consistency prior to further processing. The video acquisition module 102 then splits the received one or more videos into one or more frames. The one or more videos are split using one or more video segmentation algorithms to obtain one or more frames for further analysis. The video acquisition module 102 segments the one or more videos into the one or more frames dynamically and marks first frame of the video as a reference frame. The one or more frames are then forwarded to the region of interest detection module 104.

The region of interest detection module 104 is configured to detect one or more regions of interest within the one or more frames received from the video acquisition module 102. The one or more regions of interest include, but not limited to, eyes, cheeks, nose, lips, ears, eyebrows, hands, arms, torso, upper body, lower body, legs and feet. In an embodiment of the present invention, edge points of the one or more individuals in the one or more frames are first selected and segmented into upper body and lower body segments using active contour method. The upper body segment is further analyzed to detect face and various parts of the face. In an embodiment of the present invention, the region of interest detection module 104 uses Viola-Jones algorithm for detecting face and various parts of the face of an individual in the one or more frames of the one or more videos. Further, the Viola-Jones algorithm uses a sliding-window approach and cascaded classifiers for detecting regions of interest in the one or more frames. The upper body and lower body segments are also used for determining gait pattern of the one or more individuals. (The gait pattern analysis is discussed in detail in later sections of the specification.) The region of interest detection module 104 detects the regions of interest irrespective of the age, sex, ethnicity of the individual captured in the video. Once the regions of interest are detected for the one or more videos, the control is transferred to the video processing module 106.

The video processing module 106 communicates with the training module 108 to train the system 100. During training, the video processing module 106 receives one or more frames that are part of sample videos required for training the system 100. The sample videos comprise various expressions such as, but not limited to, happy, sad, disgust, content, surprise, clueless and angry. In an embodiment of the present invention, the one or more expressions are classified under two categories i.e. depressive and non-depressive. Each of the detected region of interest, in two successive frames of a video, displays a motion pattern that corresponds to a particular expression. Furthermore, certain regions of interest for a particular expression display a more prominent motion pattern than other regions of interest and are therefore referred to as a Dominant Motion Regions (DMRs). The motion pattern for each of the region of interest and specifically for DMRs results in a motion vector for two consecutive frames of a video. Further, a feature extraction module (not shown) residing in the video processing module 106 is configured to determine the motion vector for two consecutive frames of the video. The feature extraction module (not shown) uses optical flow algorithm for determining values of the motion vector. In an exemplary embodiment of the present invention, the optical flow algorithm uses Horn-Schunck method for determining the motion vector. The video processing module 106 stores, in the training module 108, value of each of the determined motion vectors that correspond to onset, peak and offset of each of the expression for each of the one or more detected regions of interest. The motion vectors are susceptible to change of scale and direction of motion. The feature extraction module (not shown) takes average values using multiple videos while determining and storing values of motion vectors in the training module 108 so that the stored values are independent of scale and direction of motion. The motion vectors between two frames are binned according to the primary angle along the horizontal axis and weighted with the magnitude in order to ensure that the values of motion vectors are independent of the direction of motion.

Once the values of each of the one or more motion vectors corresponding to the onset, peak and offset of each of the expression are stored, the system 100 is said to be trained to analyze the videos of the one or more individuals for predicting various expressions and neurological disorders.

The video processing module 106 is configured to analyze the detected one or more regions of interest from the one or more frames of the one or more videos of the one or more individuals for detecting depression. The analysis involves determining, by the feature extraction module (not shown), a motion vector for each of the one or more regions of interest in a set of two successive frames. For the first set of successive frames, the first frame of the video is considered as the reference frame. The analysis further involves comparing value of the motion vector for each of the one or more regions of interest with corresponding pre-stored values for each of the one or more region of interest stored in the training module 108. The comparison is performed by a comparator (not shown) residing in the video processing module 106. The comparator (not shown) is configured to compare values of the motion vectors with a pre-stored set of values to determine matching values. In an embodiment of the present invention, the comparator (not shown) comprises one or more algorithms for comparing values of the motion vectors. The video processing module 106 is further configured to identify at least one motion vector, based on the comparison, which matches the pre-stored value of the motion vector. Further, the pre-stored value of the motion vector indicates onset of an expression. The video processing module 106 also identifies a region of interest and a frame corresponding to the identified at least one motion vector associated with the onset of the indicated expression. In an embodiment of the present invention, the identified region of interest is the DMR that exhibits maximum motion pattern as compared with other regions of interest.

The feature extraction module (not shown), residing in the video processing module 106, then determines a motion vector for the identified region of interest in subsequent sets of successive frames of the one or more videos. In an embodiment of the present invention, if the video processing module 106 detects that there is a difference between the reference frame and the next frame based on the extracted motion vector for the first set of successive frames, then the next frame is considered as the reference frame for the subsequent set of successive frames to be analyzed. The comparator within the video processing module 106 then compares value of the motion vector in the subsequent sets of successive frames with at least one of: a pre-stored value of motion vector that correspond to the peak and a pre-stored value of motion vector that correspond to offset of the indicated expression. Further, the value of the motion vector is compared with the pre-stored values of motion vectors associated with the indicated expression thereby facilitating faster processing by eliminating the need of comparison of values of motion vectors of subsequent set of frames with the values of motion vectors associated with the other expressions. The video processing module 106 identifies the frames that correspond to the at least one of: the pre-stored value of motion vector that correspond to the peak and a pre-stored value of motion vector that correspond to offset of the indicated expression.

Figure 2:
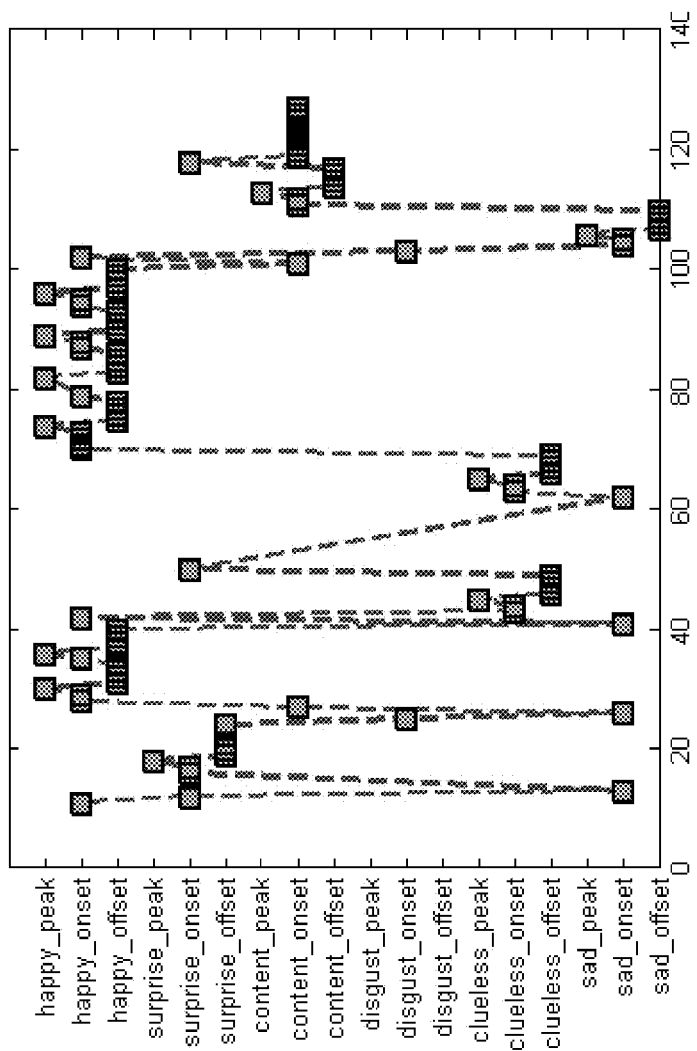
FIG. 2 represents a graph showing the onset, peak and offset of six expressions against each frame, in accordance with an exemplary embodiment of the present invention.

Once the frames comprising the motion vector for onset, peak and offset of the indicated expression are identified, the testing module 110 generates a pictorial representation in the form of, but not limited to, a graph, a histogram and a table to depict the onset, peak and offset of the indicated expression in the one or more frames of the one or more videos. Further, the video processing module 106 along with the testing module 110 continues analyzing the one or more frames beyond the frame corresponding to the offset of the indicated expression in the same manner as described above to detect all the expressions of the one or more individuals in the one or more videos. The testing module 110 then generates a pictorial representation of the entire video depicting the onset, peak and offset of all the expressions of the one or more individuals captured in the one or more videos. In an embodiment of the present invention, the testing module 110 predicts whether the one or more individuals are suffering from the one or more neurological disorders such as, but not limited to, depression based on the generated pictorial representation and prevalence of expressions that correspond to depression. In another embodiment of the present invention, the generated pictorial representation may also assist healthcare personnel in determining if the one or more individuals are suffering from depression or any other neurological disorder. In yet another embodiment of the present invention, the generated pictorial representation can be analyzed to detect a sudden change or no change in the expressions of an individual to anticipate a neurological condition of the individual. In an embodiment of the present invention, the testing module 110 may generate a graph based log of the expressions of the individual that can be used to interpret depressive tendency of the individual. FIG. 2 represents a graph showing the onset, peak and offset of six expressions against each frame, in accordance with an exemplary embodiment of the present invention.

In another embodiment of the present invention, the system 100 is capable of determining the gait patterns for predicting neurological disorders. For detecting the gait patterns, the system 100 has to be first trained. During training one or more features corresponding to one or more gait patterns are stored in the training module 108 using sample videos of subjects having known gait pattern. The one or more gait patterns include, but not limited to, parkinsonian gait, scissor gait, spastic gait, steppage gait and normal gait. The one or more features corresponding to the one or more gait patterns include, motion, posture, arm swing velocity and body balance.

Figure 3:
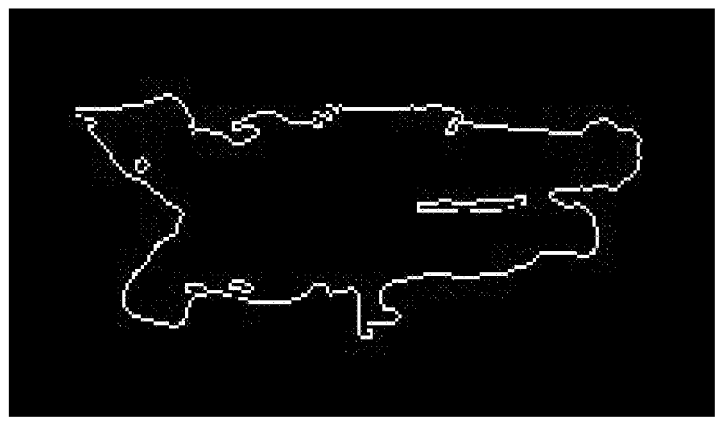
FIG. 3 illustrates two frames corresponding to subject's right leg front and left leg front while the subject is walking, in accordance with an exemplary embodiment of the present invention.
Figure 3:
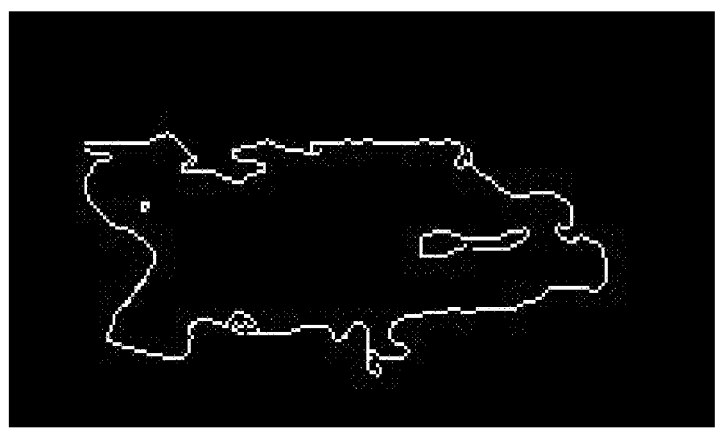

In an embodiment of the present invention, motion vector and posture vector are computed using the lower body segments of the one or more frames of subjects having known gait pattern. The lower body segment of each of the one or more frames is received from the region of interest detection module 104. The region of interest detection module 104 also labels the lower body segment of each of the one or more frames based on the subject's position of the leg with respect to the other leg. The frames in which the subject's left leg is in the front are labeled as LLF and the frames in which the subject's right leg is in the front are labeled as RLF. The frames labeled as LLF and RLF are then analyzed for computing motion vector and posture vector. FIG. 3 illustrates two frames corresponding to subject's right leg front and left leg front while the subject is walking, in accordance with an exemplary embodiment of the present invention.

Figure 4:
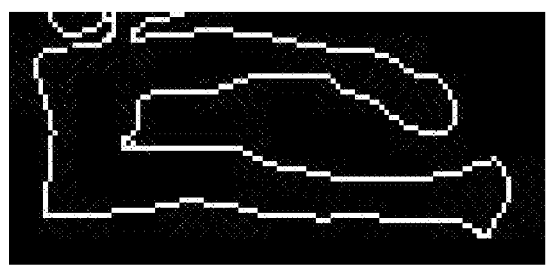
FIG. 4 illustrates contours of posture for parkinsonian gait, scissor gait and spastic gait, in accordance with an exemplary embodiment of the present invention.
Figure 4:
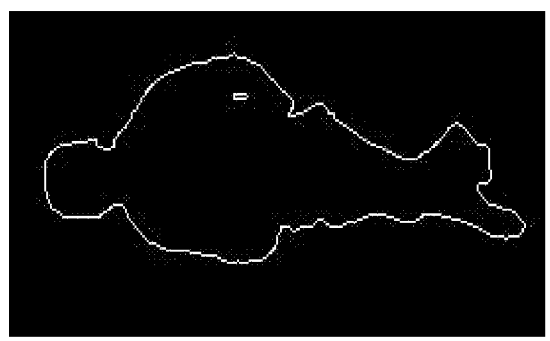
Figure 4:
Figure 5:
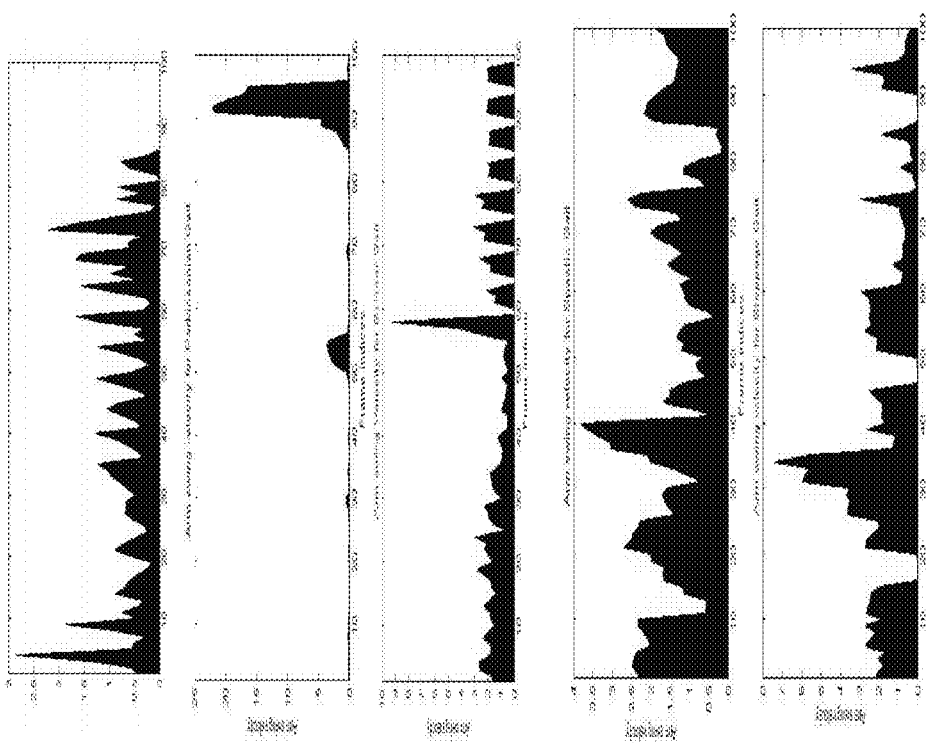
FIG. 5 represent graphs showing arm swing velocity of five different subjects having normal gait, parkinsonian gait, scissor gait, spastic gait and steppage gait, in accordance with an exemplary embodiment of the present invention.
Figure 6:
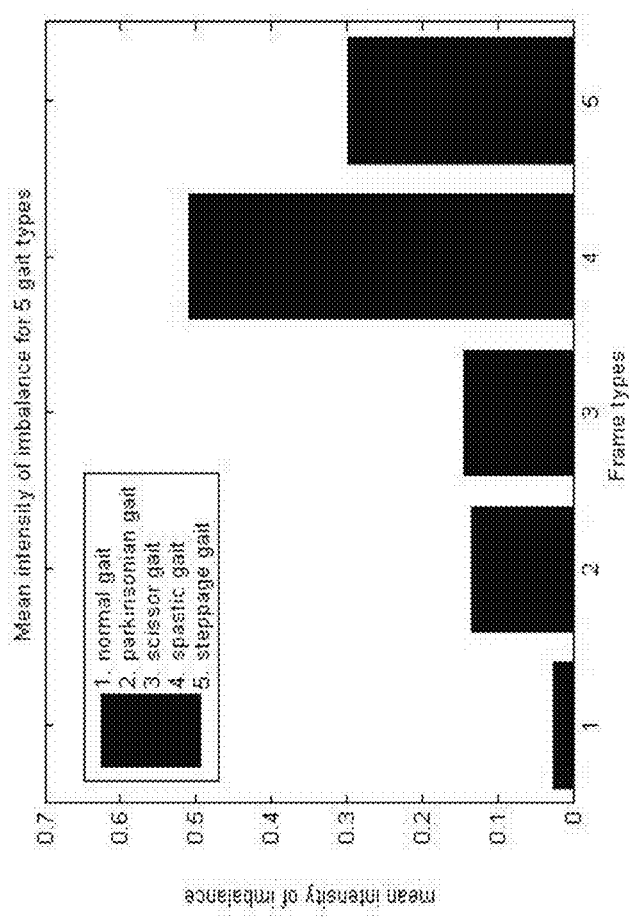
FIG. 6 represents a histogram with mean intensity of imbalance for five types of gait, in accordance with an exemplary embodiment of the present invention.

In an embodiment of the present invention, the motion vector is computed using Horn-Schunk algorithm. Further, the Horn-Schunk algorithm yields high density vectors. The motion vector is computed as a 100-dimensional vector representing a histogram of flow vectors for a set of RLF and LLF frames for each gait pattern. The posture vector is computed using two techniques i.e. global contour based technique (Fourier descriptor) and global region based technique (seven invariant moments). In an embodiment of the present invention, the upper body of the individual is tracked across a set of successive frames using Kanade-Lucas-Tomasi (KLT) feature tracker technique. The change of the shape of the upper body provides cues related to the subject's posture change. The posture feature vector is computed by analyzing the posture, when the subject changes legs while walking, across a set of successive frames. The computed posture vector is a 32-dimensional vector representing the difference of Fourier descriptor and moments between a RLF and LLF frame for each set of successive frames in which the subject is walking. The computed motion pattern and posture vectors are then stored as Gaussian Mixture Model (GMM). The stored GMM is then used for comparison to detect abnormal gait patterns in individuals. FIG. 4 illustrates contours of posture for parkinsonian gait, Scissor gait and spastic gait, in accordance with an exemplary embodiment of the present invention. Once the motion and posture vectors have been computed, other features for predicting gait pattern are computed. The arm swing velocity feature is computed by using frames of the video that have arms of the subject, while the subject is walking. Further, points on the arms are selected and then tracked across frames when the subject is walking using the optical flow algorithm. The velocity for each point is computed using the optical flow components in x and y direction to compute the arm swing velocity. Further, the computed arm swing velocity is stored for each of the gait pattern in the training module 108. FIG. 5 represent graphs showing arm swing velocity of five different subjects having normal gait, parkinsonian gait, scissor gait, spastic gait and steppage gait, in accordance with an exemplary embodiment of the present invention. The body balance feature is also computed and stored, for each gait pattern, by tracking centroid of the upper body across a set of successive frames to determine whether or not the subject is walking in a straight line. The body balance feature is then computed as intensity of imbalance. FIG. 6 represents a histogram with mean intensity of imbalance for five types of gait, in accordance with an exemplary embodiment of the present invention.

In an embodiment of the present invention, a score is assigned to each of the one or more features for each of the gait pattern. The assigned scores are then used for efficiently determining gait pattern of the one or more individuals. Once values of each of the one or more features corresponding to various gait patterns are stored, the system 100 is said to be trained to analyze the videos of the one or more individuals for predicting gait patterns.

In operation, the video acquisition module 102 receives the one or more videos of the one or more individuals, while they are walking, for determining the gait pattern. In an embodiment of the present invention, the one or more videos may have different views such as, but not limited to, front view, side view and back view of the one or more individuals. The video is then split into the one or more frames by the video acquisition module 102. Further, the one or more frames are sent to region of interest detection module 104 to detect the one or more regions of interest such as, but not limited to, right leg, left leg, arms and upper body within the one or more frames. Once the one or more regions of interest are detected, the control is transferred to the video processing module 106. The video processing module 106 computes the motion and posture vectors as GMM and compares with the pre-stored GMM for each of the gait patterns stored in the training module 108. The video processing module 106 also computes values corresponding to the arm swing velocity and body balance. The video processing module 106 then compares the computed values with pre-stored values of the arm swing velocity and body balance for each of the gait patterns. Based on the comparison, the video processing module 106 identifies the type of gait pattern corresponding to pre-stored values of the one or more features that match with corresponding computed values of the one or more features. Further, the video processing module 106 also determines the degree of abnormality of gait pattern based on the comparison. In an embodiment of the present invention, a score is computed by the video processing module 106 based on the computed values of the one or more features for each of the one or more analyzed videos. The computed score is compared with the pre-assigned scores that correspond to a type of gait pattern thereby facilitating efficient determination of the gait pattern of the one or more individuals in the one or more analyzed videos. The results of the analysis comprising determination of the gait pattern is presented in the form of, but not limited to, graphs, histograms and any other pictorial form by the testing module 110. In an embodiment of the present invention, the system 100 can be used for security applications wherein the individual's gait pattern can be used for identification purposes. In another embodiment of the present invention, the system 100 is used for detecting movement and tremors in an individual. In an exemplary embodiment of the present invention, detection of tremors and fine movements is often required during lie detector test to detect if the person undergoing the test is lying.

Figure 7A:
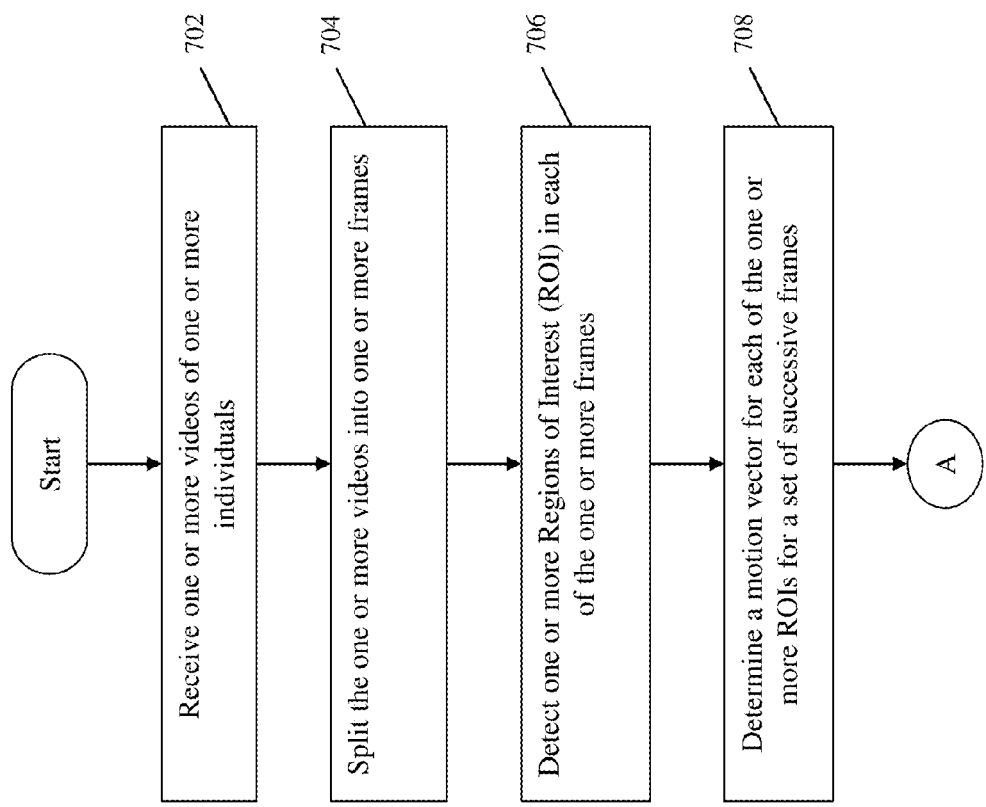
FIGS. 7A, 7B and 7C represent a flowchart illustrating a method for predicting one or more neurological disorders, in accordance with an embodiment of the present invention.
Figure 7B:
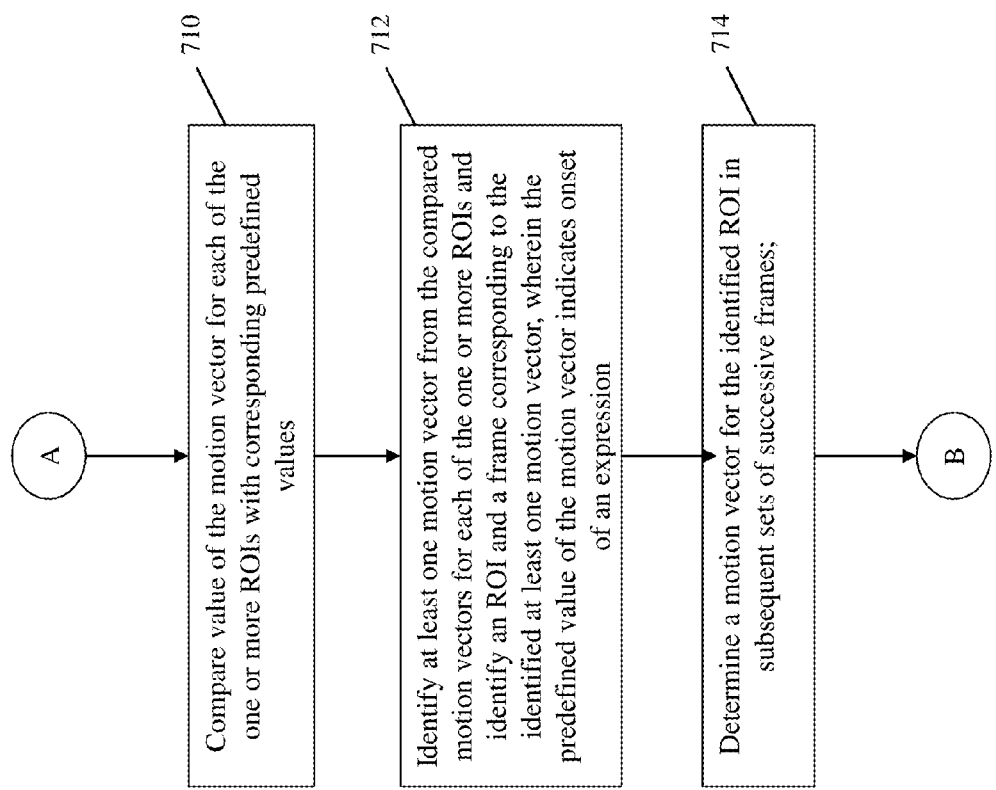
Figure 7C:
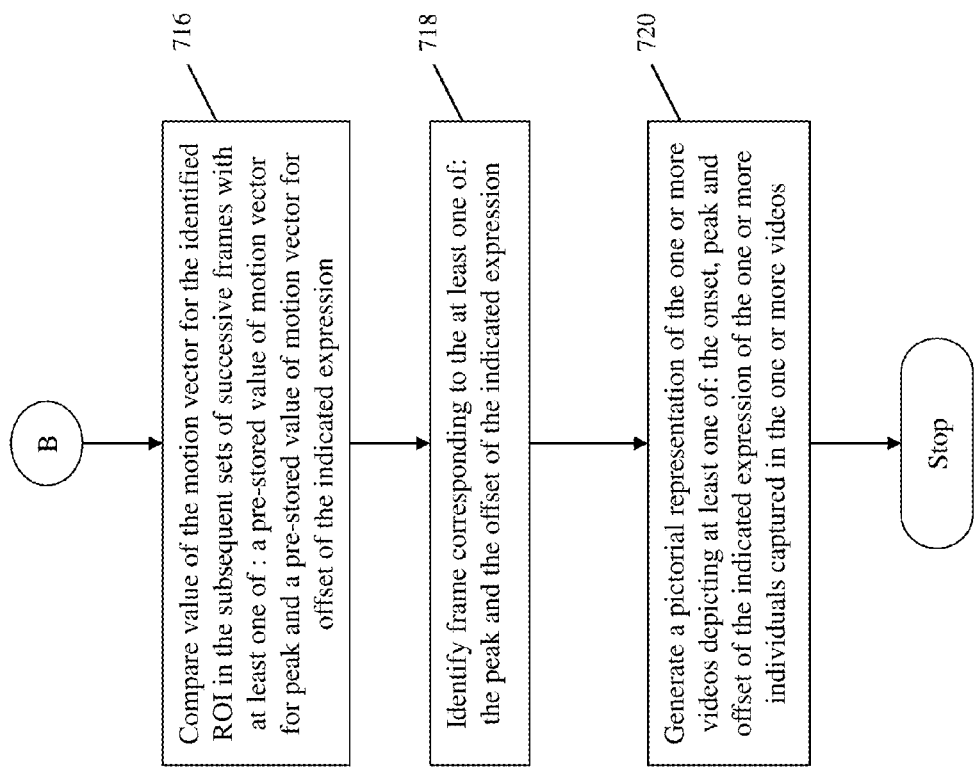

FIGS. 7A and 7B represent a flowchart illustrating a method for predicting one or more neurological disorders, in accordance with an embodiment of the present invention.

At step 702, one or more videos of one or more individuals are received. In an embodiment of the present invention, the one or more videos of the one or more individuals include videos of subjects whose expressions are to be analyzed and based on the analysis disorder has to be predicted. Further, the one or more videos may be captured when the individual/subject in the one or more videos is involved in an activity such as, but not limited to, speaking, walking, running and/or any other activity. In an embodiment of the present invention, one or more expressions include at least one of: happy, content, sad, disgust, surprise, clueless and angry. In an embodiment of the present invention, the one or more videos are received from one or more electronic devices such as, but not limited to, a mobile phone, a tablet, a camera or any other device having a camera capable of capturing videos.

At step 704, the received one or more videos are split into one or more frames. The one or more videos are split using one or more video segmentation algorithms to obtain one or more frames for further analysis. Prior to splitting, the resolution and illumination of the one or more videos is balanced as the one or more videos are captured by varied sources. This helps in maintaining the quality of the one or more videos for consistency prior to splitting.

At step 706, one or more regions of interest in each of the one or more frames are detected. The one or more regions of interest include, but not limited, eyes, cheeks, nose, lips, ears, eyebrows, hands, arms, torso, upper body, lower body, legs and feet. In an embodiment of the present invention, face and various parts of the face of an individual in the one or more frames are detected using Viola-Jones algorithm. Further, the Viola-Jones algorithm uses a sliding-window approach and cascaded classifiers for detecting regions of interest in the one or more frames. Once the one or more regions of interest are detected, each of the one or more detected regions of interest in each of the one or more frames are analyzed in subsequent steps.

At step 708, a motion vector, for each of the one or more detected regions of interest, in a set of successive frames is determined. In an embodiment of the present invention, the motion vector for each of the one or more detected regions of interest is determined using an optical flow algorithm. In an exemplary embodiment of the present invention, the optical flow algorithm uses Horn-Schunck method for determining the motion vector.

At step 710, value of the determined motion vector for each of the one or more regions of interest is compared with corresponding pre-stored values of the motion vector of the one or more regions of interest. In an embodiment of the present invention, the pre-stored values of the motion vector of the one or more regions of interest are stored at the time of configuration using the sample videos. During configuration, one or more frames that are part of the sample videos are received. The sample videos comprise various expressions such as, but not limited to, happy, sad, disgust, content, surprise, angry and clueless. In an embodiment of the present invention, the one or more expressions are classified under two categories i.e. depressive and non-depressive. Further, each of the detected region of interest, in two successive frames of a video, displays a motion pattern that corresponds to a particular expression. Furthermore, certain regions of interest for a particular expression display a more prominent motion pattern than other regions of interest and are therefore referred to as a Dominant Motion Regions (DMRs). The motion pattern for each region of interest and specifically for DMRs results in a motion vector by comparing two successive frames of a video. In an embodiment of the present invention, the motion vector may be estimated using the Horn-Schunck optical flow algorithm. Further, value of each of the motion vectors that correspond to onset, peak and offset of each of the expression for each of the one or more detected regions of interest is determined and stored. Once the values of each of the one or more motion vectors corresponding to the onset, peak and offset of each of the expression are stored, the videos of the one or more individuals are analyzed for predicting various expressions and neurological disorders.

At step 712, at least one motion vector, from the determined and compared motion vectors for each of the one or more regions of interest, is identified based on the comparison at step 710. The at least one motion vector is identified as the value of the identified motion vector matches with a pre-stored value of the motion vector. Further, the pre-stored value of the motion vector indicates onset of an expression. Furthermore, a region of interest and a frame corresponding to the identified at least one motion vector are also identified.

At step 714, one or more motion vectors for the identified region of interest in subsequent sets of successive frames are determined. In an embodiment of the present invention, the motion vectors are determined using the optical flow algorithm. In an exemplary embodiment of the present invention, the optical flow algorithm uses Horn-Schunck method for determining the motion vector.

At step 716, value of each of the one or more motion vectors for the identified region of interest in the subsequent sets of successive frames is compared with at least one of: a pre-stored value of motion vector that correspond to peak and a pre-stored value of motion vector that correspond to offset of the indicated expression. Further, the value of the motion vector is compared with the pre-stored values of motion vectors associated only with the indicated expression thereby facilitating faster processing by eliminating the need of comparison with the values of motion vectors associated with the other expressions.

At step 718, a frame corresponding to the at least one of: the peak of the indicated expression and the offset of the indicated expression is identified.

At step 720, a pictorial representation of the one or more videos depicting at least one of: the onset, peak and offset of the indicated expression of the one or more individuals captured in the one or more videos is generated. In the similar manner as described in previous steps, the one or more frames beyond the frame corresponding to the offset of the indicated expression are analyzed to detect all the expressions in an entire video. A pictorial representation of the entire video depicting the onset, peak and offset of all the expressions is also generated. In an embodiment of the present invention, the generated pictorial representation may assist healthcare personnel in determining if the one or more individuals are suffering from depression or any other neurological disorder. In another embodiment of the present invention, the generated pictorial representation is used for predicting the one or more neurological disorders such as, but not limited to, depression based on the expressions of the one or more individuals. In yet another embodiment of the present invention, the generated pictorial representation can be analyzed to detect a sudden change or no change in the expressions of an individual to anticipate a neurological condition of the individual. In an embodiment of the present invention, a graph based log of the expressions of the individual is generated that can be used to interpret depressive tendency of the individual.

In another embodiment of the present invention, the one or more videos of the one or more individuals are analyzed for determining abnormal gait pattern and predicting associated neurological diseases.

For detecting abnormal gait patterns, one or more features corresponding to one or more gait patterns are first stored using sample videos of subjects having known gait pattern. The one or more gait patterns include, but not limited to, parkinsonian gait, scissor gait, spastic gait, steppage gait and normal gait. The one or more features corresponding to the one or more gait patterns include, motion, posture, arm swing velocity and body balance.

Once values of each of the one or more features corresponding to various gait patterns are stored, videos of the one or more individuals are received for analysis and identifying the one or more gait patterns based on the analysis. In an embodiment of the present invention, the one or more received videos may have different views such as, but not limited to, front view, side view and back view of the one or more individuals while they are walking. Further, the one or more videos are split into the one or more frames. Furthermore, the one or more regions of interest such as, but not limited to, right leg, left leg, arms and upper body are then detected within the one or more frames. Each of the one or more regions of interest are then analyzed to determine one or more features related to the one or more gait patterns in a set of successive frames. Further, the values of the determined one or more features are compared with the corresponding pre-stored values of the one or more features of each of the one or more regions of interest. In an embodiment of the present invention, the motion and posture vectors, associated with the motion and posture feature respectively, are computed as Gaussian Mixture Model (GMM) for a set of successive frames and compared with pre-stored GMM for each of the gait patterns. Values of arm swing velocity and body balance feature are also computed and compared with pre-stored values of the arm swing velocity and body balance feature for each of the gait patterns. Based on the comparison, the type of gait pattern, associated with a pre-stored value of the one or more features that match with at least one corresponding value of the one or more determined features, is identified. Further, the degree of abnormality of gait pattern is also determined based on the comparison. The results of the analysis comprising determination of the gait pattern is provided in the form of, but not limited to, graphs, histograms and any other pictorial form which are used for predicting the one or more neurological disorders.

Figure 8:
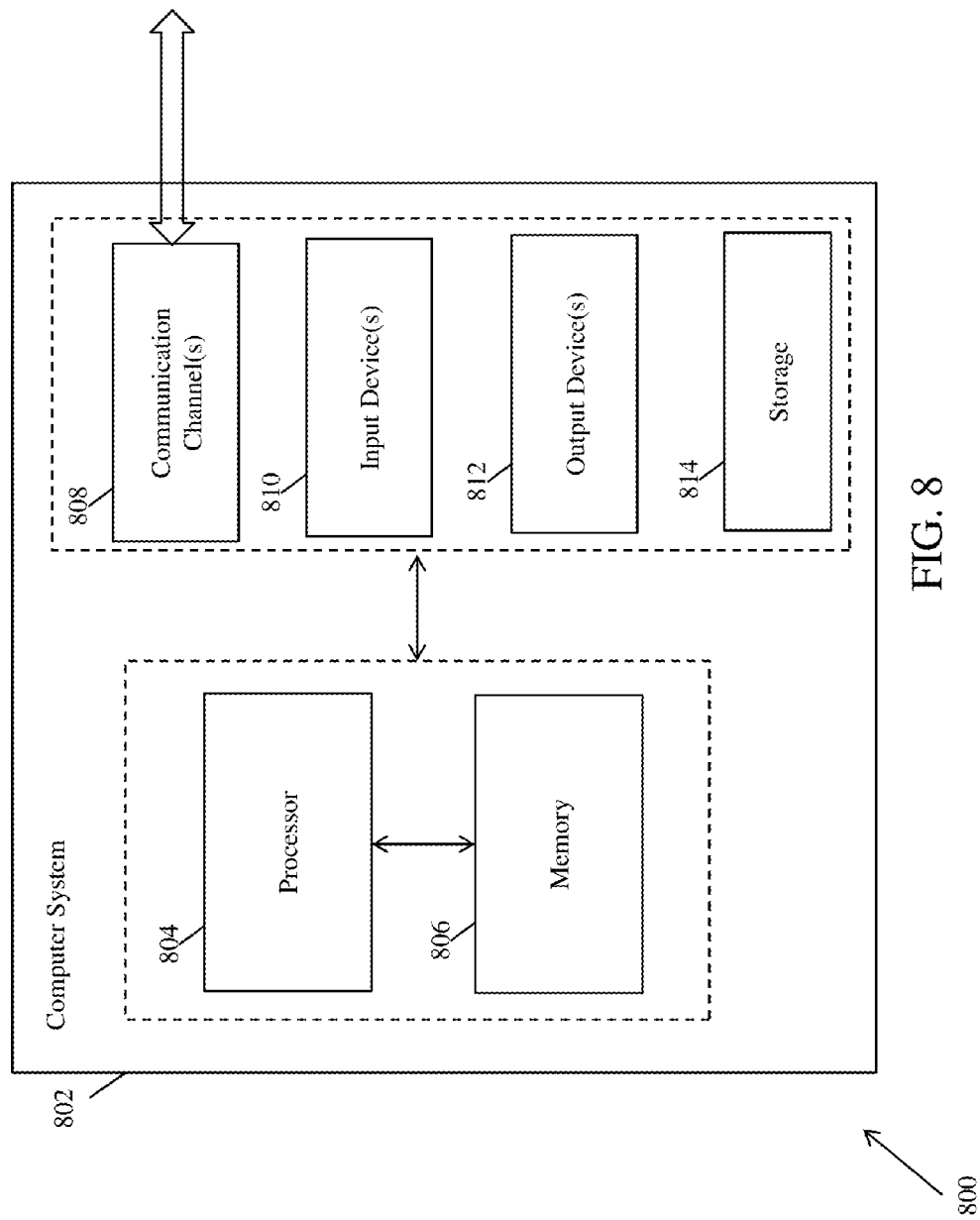
FIG. 8 illustrates an exemplary computer system for predicting one or more neurological disorders, in accordance with an embodiment of the present invention.

FIG. 8 illustrates an exemplary computer system for predicting one or more neurological disorders, in accordance with an embodiment of the present invention.

The computer system 802 comprises a processor 804 and a memory 806. The processor 804 executes program instructions and may be a real processor. The processor 804 may also be a virtual processor. The computer system 802 is not intended to suggest any limitation as to scope of use or functionality of described embodiments. For example, the computer system 802 may include, but not limited to, a general-purpose computer, a programmed microprocessor, a micro-controller, a peripheral integrated circuit element, and other devices or arrangements of devices that are capable of implementing the steps that constitute the method of the present invention. In an embodiment of the present invention, the memory 806 may store software for implementing various embodiments of the present invention. The computer system 802 may have additional components. For example, the computer system 802 includes one or more communication channels 808, one or more input devices 810, one or more output devices 812, and storage 814. An interconnection mechanism (not shown) such as a bus, controller, or network, interconnects the components of the computer system 802. In various embodiments of the present invention, operating system software (not shown) provides an operating environment for various softwares executing in the computer system 802, and manages different functionalities of the components of the computer system 802.

The communication channel(s) 808 allow communication over a communication medium to various other computing entities. The communication medium provides information such as program instructions, or other data in a communication media. The communication media includes, but not limited to, wired or wireless methodologies implemented with an electrical, optical, RF, infrared, acoustic, microwave, bluetooth or other transmission media.

The input device(s) 810 may include, but not limited to, a keyboard, mouse, pen, joystick, trackball, a voice device, a scanning device, or any another device that is capable of providing input to the computer system 802. In an embodiment of the present invention, the input device(s) 810 may be a sound card or similar device that accepts audio input in analog or digital form. The output device(s) 812 may include, but not limited to, a user interface on CRT or LCD, printer, speaker, CD/DVD writer, or any other device that provides output from the computer system 802.

The storage 814 may include, but not limited to, magnetic disks, magnetic tapes, CD-ROMs, CD-RWs, DVDs, flash drives or any other medium which can be used to store information and can be accessed by the computer system 802. In various embodiments of the present invention, the storage 814 contains program instructions for implementing the described embodiments.

The present invention may suitably be embodied as a computer program product for use with the computer system 802. The method described herein is typically implemented as a computer program product, comprising a set of program instructions which is executed by the computer system 802 or any other similar device. The set of program instructions may be a series of computer readable codes stored on a tangible medium, such as a computer readable storage medium (storage 814), for example, diskette, CD-ROM, ROM, flash drives or hard disk, or transmittable to the computer system 802, via a modem or other interface device, over either a tangible medium, including but not limited to optical or analogue communications channel(s) 808. The implementation of the invention as a computer program product may be in an intangible form using wireless techniques, including but not limited to microwave, infrared, bluetooth or other transmission techniques. These instructions can be preloaded into a system or recorded on a storage medium such as a CD-ROM, or made available for downloading over a network such as the internet or a mobile telephone network. The series of computer readable instructions may embody all or part of the functionality previously described herein.

The present invention may be implemented in numerous ways including as an apparatus, method, or a computer program product such as a computer readable storage medium or a computer network wherein programming instructions are communicated from a remote location.

While the exemplary embodiments of the present invention are described and illustrated herein, it will be appreciated that they are merely illustrative. It will be understood by those skilled in the art that various modifications in form and detail may be made therein without departing from or offending the spirit and scope of the invention as defined by the appended claims.

We claim:

1. A method for predicting one or more neurological disorders via a processor configured to execute program instructions stored in a memory, the method comprising:
receiving, via the processor, one or more videos of one or more individuals;
splitting, via the processor, the one or more videos into one or more frames;
detecting, via the processor, one or more regions of interest in each of the one or more frames;
analyzing, via the processor, each of the one or more regions of interest in each of the one or more frames by:
determining a motion vector for each of the one or more regions of interest in a set of successive frames; and
comparing value of the determined motion vector for each of the one or more regions of interest with corresponding pre-stored values, wherein the pre-stored values for the motion vector for each of the one or more regions are pre-stored in a database;
identifying, via the processor, at least one motion vector, from the determined motion vectors, that matches with a pre-stored value of a motion vector thereby identifying a region of interest and a frame corresponding to the identified at least one motion vector, wherein the pre-stored value indicates onset of an expression;
determining, via the processor, one or more motion vectors for the identified region of interest in subsequent sets of successive frames;
comparing, via the processor, value of the one or more determined motion vectors for the identified region of interest with at least one of a pre-stored value of motion vector corresponding to peak of an indicated expression and a pre-stored value of motion vector corresponding to offset of the indicated expression, wherein the peak of the indicated expression and the offset of the indicated expression are values in at least one of a graph, a histogram and a table depicting the indicated expression;
identifying, via the processor, the frame corresponding to the at least one of: the peak of the indicated expression and the offset of the indicated expression; and
generating, via the processor, a pictorial representation of the one or more videos depicting at least one of: the onset, peak and offset of the indicated expression of the one or more individuals captured in the one or more videos for predicting the one or more neurological disorders.

2. The method of claim 1, wherein the one or more expressions include at least one of: happy, content, sad, disgust, surprise, clueless and angry.

3. The method of claim 1, wherein the detected one or more regions of interest include at least one of: eyes, cheeks, nose, lips, ears, eyebrows, hands, arms, torso, legs and feet.

4. The method of claim 1, wherein the regions of interest are detected using Viola-Jones algorithm.

5. The method of claim 1, wherein the motion vector for each of the one or more regions of interest in a set of successive frames is determined using optical flow algorithm.

6. The method of claim 5, wherein the optical flow algorithm uses Horn-Schunck method for determining the motion vector.

7. The method of claim 1, wherein the one or more individuals are speaking while the one or more videos are being captured.

8. A system for predicting one or more neurological disorders, the system comprising:
a video acquisition module configured to:
receive one or more videos of one or more individuals; and
split the one or more videos into one or more frames;
a region of interest detection module configured to detect one or more regions of interest in each of the one or more frames;
a video processing module configured to analyze each of the one or more detected regions of interest in each of the one or more frames, wherein the video processing module comprises:
a feature extraction module configured to determine a motion vector for each of the one or more regions of interest in a set of successive frames; and
a comparator configured to compare value of the determined motion vector for each of the one or more regions of interest with corresponding pre-stored values, wherein the pre-stored values for the motion vector for each of the one or more regions are stored in a training module;
the feature extraction module further configured to:
identify at least one motion vector, from the determined motion vectors, that matches with a pre-stored value of a motion vector thereby identifying a region of interest and a frame corresponding to the identified at least one motion vector, wherein the pre-stored value indicates onset of an expression; and determine one or more motion vectors for the identified region of interest in subsequent sets of successive frames;
the comparator further configured to:
compare value of the one or more determined motion vectors for the identified region of interest with at least one of a pre-stored value of motion vector corresponding to peak of an indicated expression and a pre-stored value of motion vector corresponding to offset of the indicated expression, wherein the peak of the indicated expression and the offset of the indicated expression are values in at least one of a graph, a histogram and a table depicting the indicated expression; and
identify the frame corresponding to the at least one of: the peak of the indicated expression and the offset of the indicated expression; and
a testing module configured to generate a pictorial representation of the one or more videos depicting at least one of: the onset, peak and offset of the indicated expression of the one or more individuals captured in the one or more videos for predicting the one or more neurological disorders.

9. The system of claim 8, wherein the one or more expressions include at least one of: happy, content, sad, disgust, surprise, clueless and angry.

10. The system of claim 8, wherein the detected one or more regions of interest include at least one of: eyes, cheeks, nose, lips, ears, eyebrows, hands, arms, torso, legs and feet.

11. The system of claim 8, wherein the regions of interest are detected using Viola-Jones algorithm.

12. The system of claim 8, wherein the motion vector for each of the one or more regions of interest in a set of successive frames is determined using optical flow algorithm.

13. The system of claim 12, wherein the optical flow algorithm uses Horn-Schunck method for determining the motion vector.

14. The system of claim 8, wherein the one or more individuals are speaking while the one or more videos are being captured.

15. A computer program product for predicting one or more neurological disorders, the computer program product comprising:
 a non-transitory computer-readable medium having computer-readable program code stored thereon, the computer-readable program code comprising instructions that when executed by a processor, cause the processor to:
 receive one or more videos of one or more individuals;
 split the one or more videos into one or more frames:
 detect one or more regions of interest in each of the one or more frames;
 analyze each of the one or more regions of interest in each of the one or more frames by:
  determining a motion vector for each of the one or more regions of interest in a set of successive frames; and
  comparing value of the determined motion vector for each of the one or more regions of interest with corresponding pre-stored values, wherein the pre-stored values for the motion vector for each of the one or more regions are pre-stored in a database;
 identify at least one motion vector, from the determined motion vectors, that matches with a pre-stored value of a motion vector thereby identifying a region of interest and a frame corresponding to the identified at least one motion vector, wherein the pre-stored value indicates onset of an expression;
 determine one or more motion vectors for the identified region of interest in subsequent sets of successive frames;
 compare value of the one or more determined motion vectors for the identified region of interest with at least one of a pre-stored value of motion vector corresponding to peak of an indicated expression and a pre-stored value of motion vector corresponding to offset of the indicated expression, wherein the peak of the indicated expression and the offset of the indicated expression are values in at least one of a graph, a histogram and a table depicting the indicated expression;
 identify the frame corresponding to the at least one of: the peak of the indicated expression and the offset of the indicated expression; and
 generate a pictorial representation of the one or more videos depicting at least one of: the onset, peak and offset of the indicated expression of the one or more individuals captured in the one or more videos for predicting the one or more neurological disorders.

* * * * *